United States Patent
Stonisch

(10) Patent No.: US 8,043,092 B2
(45) Date of Patent: *Oct. 25, 2011

(54) DEMONSTRATION DENTAL TEMPLATE AND MATCHING TEMPORARY OVERLAY

(76) Inventor: Mary Sue Stonisch, Grosse Pointe Woods, MI (US)

( * ) Notice: Subject to any disclaimer, the term of this patent is extended or adjusted under 35 U.S.C. 154(b) by 249 days.

This patent is subject to a terminal disclaimer.

(21) Appl. No.: 12/079,386

(22) Filed: Mar. 26, 2008

(65) Prior Publication Data

US 2008/0176189 A1    Jul. 24, 2008

Related U.S. Application Data

(63) Continuation-in-part of application No. 11/226,113, filed on Sep. 14, 2005, now Pat. No. 7,520,747, which is a continuation-in-part of application No. 11/096,602, filed on Apr. 1, 2005, now abandoned.

(51) Int. Cl.
*A61C 5/00* (2006.01)

(52) U.S. Cl. ......................................... 433/215; 433/196

(58) Field of Classification Search .................. 433/167, 433/196, 215, 218, 219, 229
See application file for complete search history.

(56) References Cited

U.S. PATENT DOCUMENTS

| | | | |
|---|---|---|---|
| 1,654,387 A | 12/1927 | Stenz | |
| 2,169,719 A | 8/1939 | Bush | |
| 2,789,353 A | 4/1957 | Biggs | |
| 3,763,564 A * | 10/1973 | Petrelli et al. | 433/217.1 |
| 4,015,332 A | 4/1977 | Manne | |
| 4,226,593 A | 10/1980 | Cohen et al. | |
| 4,247,287 A | 1/1981 | Gigante | |
| 4,583,947 A | 4/1986 | Hazar | |
| 4,678,435 A | 7/1987 | Long | |
| 4,710,127 A | 12/1987 | Bellavia et al. | |
| 4,778,386 A | 10/1988 | Spiry | |
| 4,906,186 A | 3/1990 | France, Jr. | |
| 5,378,737 A | 1/1995 | Jacobs et al. | |
| 5,385,469 A | 1/1995 | Weissman | |
| 5,458,489 A | 10/1995 | Tennyson | |
| 5,547,381 A * | 8/1996 | Nutting | 433/219 |
| 5,569,036 A | 10/1996 | Goldiner et al. | |
| 5,639,235 A | 6/1997 | Lapointe et al. | |
| 5,775,909 A | 7/1998 | Langer | |
| 5,803,737 A | 9/1998 | Lyalin | |

(Continued)

FOREIGN PATENT DOCUMENTS

DE    199 19 376 A1 * 11/2000

(Continued)

OTHER PUBLICATIONS

Website Literature, Fake Teeth Styles in Hardwear, website-www.drbukk.com/bukkstyles.html., 7 pages, printed from website Dec. 10, 2004.

(Continued)

*Primary Examiner* — Ralph Lewis

(74) *Attorney, Agent, or Firm* — Reising Ethington P.C.

(57) ABSTRACT

A dental prosthesis or template (10) simulates the front surfaces of a patient's teeth and is positioned to overlay over a patient's natural teeth (40) to provide an indication of what a dental porcelain overlay may look like once applied to the patient's teeth. A matching temporary veneer overlay (110) with simulated matching teeth sized and shaped to the template is constructed to be installed over the patient's prepared teeth.

11 Claims, 6 Drawing Sheets

U.S. PATENT DOCUMENTS

| | | | |
|---|---|---|---|
| 5,894,017 | A | 4/1999 | Sagel et al. |
| 5,904,481 | A | 5/1999 | Shima |
| 5,916,653 | A | 6/1999 | Kunstadter et al. |
| 5,927,984 | A | 7/1999 | Lin |
| 5,951,291 | A | 9/1999 | Albert et al. |
| 6,063,830 | A | 5/2000 | Deguchi et al. |
| 6,068,481 | A | 5/2000 | Worthington |
| 6,398,550 | B1 | 6/2002 | Caritg |
| 6,422,864 | B1 | 7/2002 | Glatt |
| 6,447,296 | B2 | 9/2002 | Worthington |
| 6,820,623 | B2 | 11/2004 | Cook |
| 7,118,375 | B2 | 10/2006 | Durbin et al. |
| 7,128,572 | B2 | 10/2006 | Lauciello et al. |
| 7,153,131 | B2 | 12/2006 | Crohn |
| 7,175,427 | B2 | 2/2007 | Smith |
| 7,357,637 | B2 * | 4/2008 | Liechtung ............ 433/167 |
| 7,520,747 | B2 * | 4/2009 | Stonisch ............ 433/215 |
| 2001/0036618 | A1 * | 11/2001 | Worthington ............ 433/183 |
| 2004/0166463 | A1 | 8/2004 | Wen et al. |
| 2004/0229185 | A1 | 11/2004 | Knopp |
| 2005/0014109 | A1 | 1/2005 | Lim |
| 2005/0042569 | A1 | 2/2005 | Phan et al. |
| 2005/0196728 | A1 | 9/2005 | Goldiner |
| 2005/0227204 | A1 * | 10/2005 | Hauck ............ 433/218 |
| 2007/0009855 | A1 | 1/2007 | Stonisch |
| 2007/0059667 | A1 | 3/2007 | Lim |

FOREIGN PATENT DOCUMENTS

WO    WO 03/049569 A1 *   6/2003

OTHER PUBLICATIONS

International Search Report and Written Opinion for PCT/US06/35464, Filing Date: Sep. 12, 2006, Date of Mailing: Mar. 15, 2007, 9 pages.

* cited by examiner

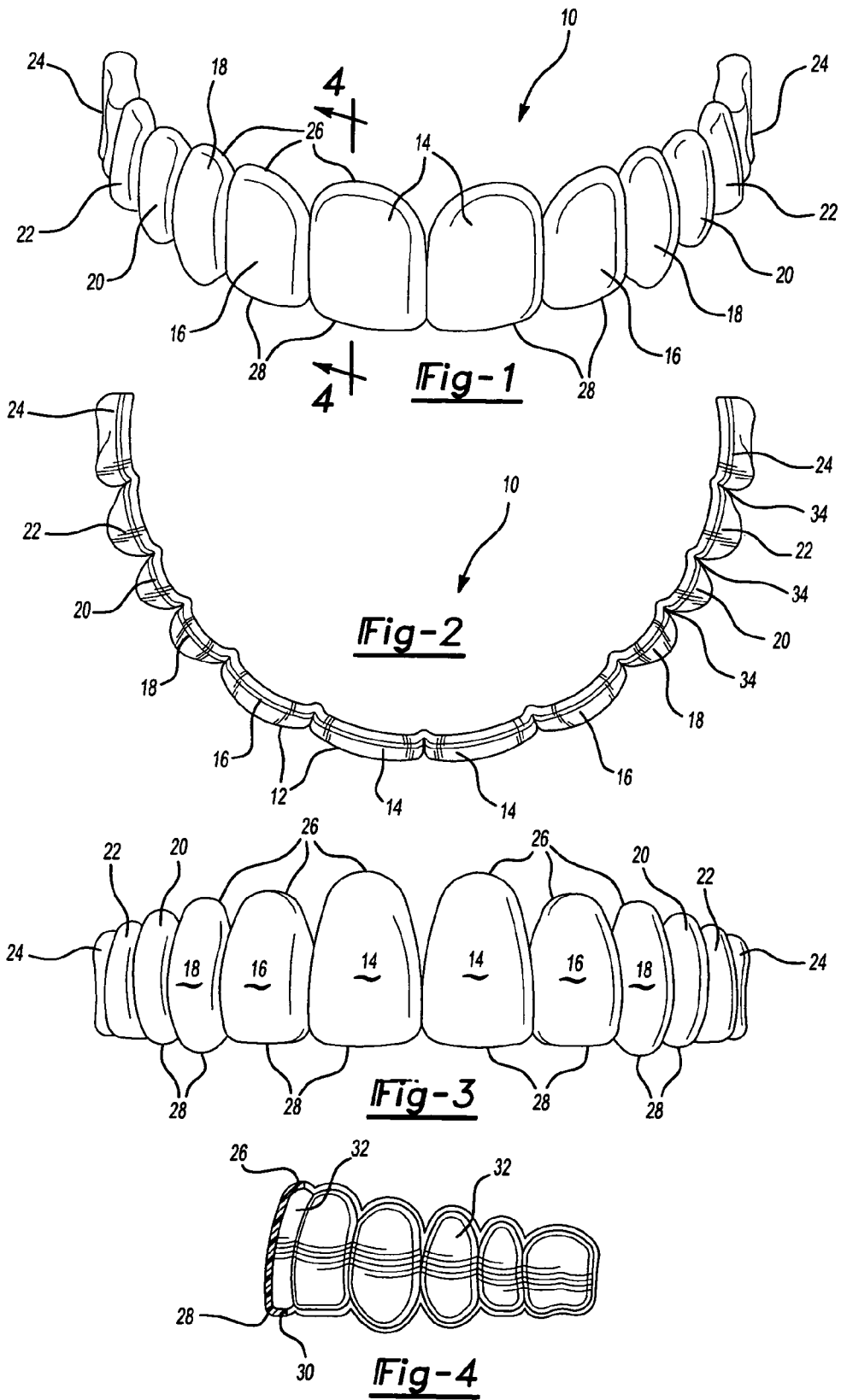

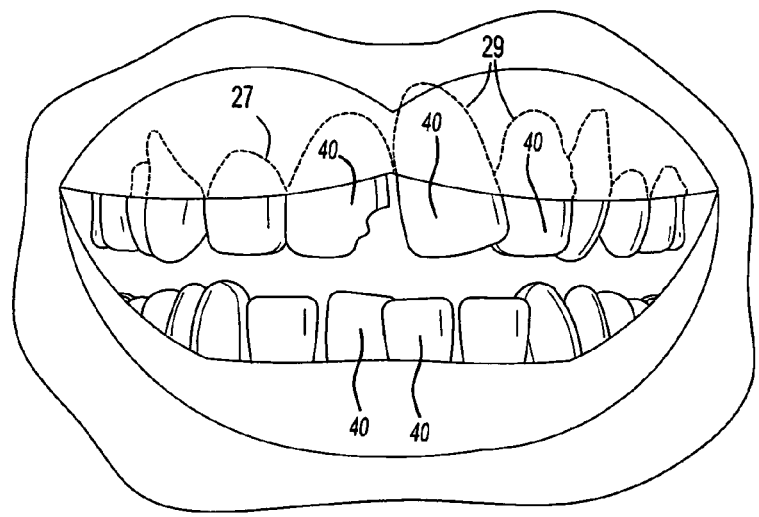
*Fig-5*
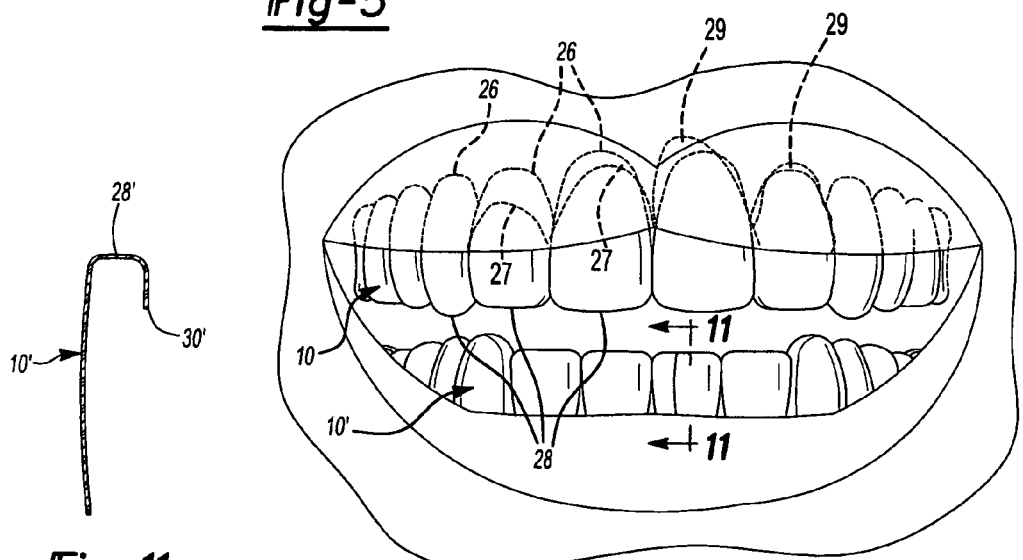
*Fig-11*
*Fig-6*
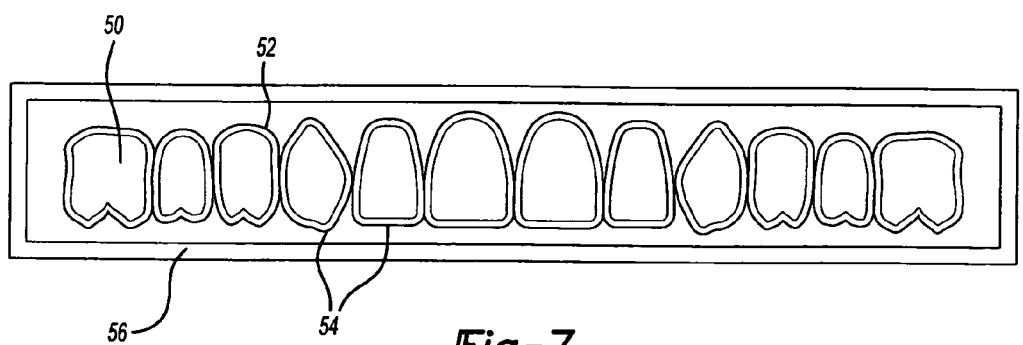
*Fig-7*

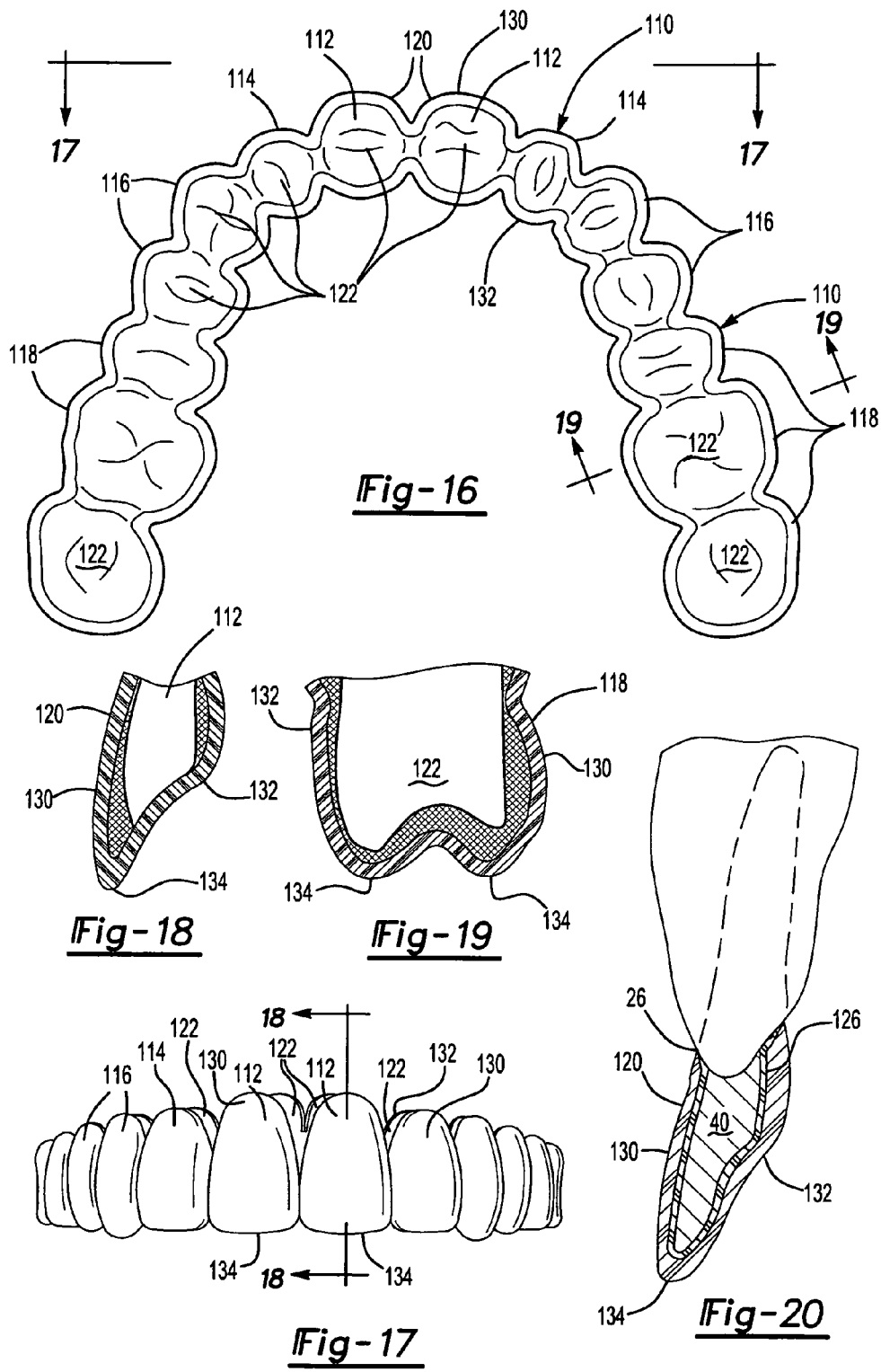

DEMONSTRATION DENTAL TEMPLATE AND MATCHING TEMPORARY OVERLAY

This application is a continuation-in-part of U.S. Ser. No. 11/226,113 filed on Sep. 14, 2005 now U.S. Pat. No. 7,520,747, which is a continuation-in-part of abandoned U.S. Ser. No. 11/096,602 filed on Apr. 1, 2005.

TECHNICAL FIELD

The field of this invention relates to demonstration dental templates and a method for providing a visual representation to a dental patient of a potential overlay along with a temporary overlay for a dental patient.

BACKGROUND OF THE DISCLOSURE

Human beings are a social animal and a person's face communicates important information to other people. A smile is a very important part of human communication and socialization. A genuine broad smile can help a person fit in and makes others who see the smile comfortable and even happy by seeing someone else's smile.

Teeth are an important part of a person's smile. Unattractive teeth or defects in a person's teeth can detract from the overall appearance of the smile. Dentists have long improved defective teeth with a porcelain overlay to enlarge, straighten, brighten, or fill in breaks or gaps in a person's teeth. A person who has excessively small teeth in part to excessive gums can enlarge the teeth by recontouring the gum line with the removal of some gum tissue in conjunction with a new overlay. People with yellow teeth or dark stains in their teeth can brighten their smile with a brighter whiter porcelain overlay.

As important as a smile is, many people with serious and unsightly defects in their smile decline to have a porcelain overlay to improve the smile for various reasons. One of these reasons is that a person may not be willing to undergo a permanent and irreversible operation unless there is a high assurance in the person's mind that the procedure will greatly enhance one's smile and the overlay will be comfortable in the mouth against one's natural teeth. The person may not have the vision or knowledge as to how such an overlay can improve one's smile. A person may initially resist the incorporation of dental prosthesis by being under the impression that the prosthesis may be uncomfortable in the mouth. Dentists until now had no easy method to demonstrate how such an overlay can improve the smile or to counteract the fears of discomfort. As such, only a limited amount of potential consumers accept and undergo an overlay procedure even though this dental treatment could greatly benefit a vastly wider consumer group.

A patient may not be willing to undergo a permanent dental procedure such as an overlay until he/she is fully assured with the knowledge that the procedure is right for him/her and will produce some dramatic and known result. The patient needs to see the image of his/her own face and smile in a dynamic setting in a more three dimensional demonstration in order to obtain the needed assurance to undergo the permanent porcelain overlay.

Recently, efforts have been made to visually demonstrate to the patient how a porcelain overlay may improve one's smile. One such attempt is to take a photograph of a person smiling and then digitally alter the teeth to produce the desired smile improvement. While the digitization can produce a number of different looks by digitally altering the teeth in a variety of ways, this process is less than optimal. The result produces a somewhat static and two dimensional look to the patient. It also gives no knowledge to the consumer related to the comfort of a porcelain overlay in the mouth.

Attempts have been made to place a temporary molded overlay of an individual tooth on a person's tooth. The overlay may adhere to the natural tooth for a short period of time in order to demonstrate to others the benefits and potential outcome of enhancing one's teeth for a better smile. The temporary molded overlay is made from a temporary moldable putty formed over a model of the desired smile changes. This putty is relined with an acrylic that is cured or glued onto a patient's teeth. A second approach is via direct sculpting composite on the surface of the patient's tooth and curing the composite in place one the desired shape has been sculpted. While these methods can provide the dynamic and three dimensional demonstration needed for the potential dental patient, they are time consuming and costly procedures for fitting a plurality of teeth.

Once a patient decides to undergo cosmetic dentistry and obtain a porcelain overlay, the patient's teeth are prepared to receive the overlay. The overlay is then made using a mold impression of the prepared teeth. The mold contains the impression of the teeth along the tooth plane however, the mold often does not provide adequate information as to the vertical and horizontal inclinations and facial planes with respect to the tooth plane to provide the best location of the outer surface of the overlay. Often, the appearance of the overlay teeth needs to be aligned with a facial plane that is angled with respect to the plane of the natural teeth for the best appearance. Dentists have in the past approximated the best angle by placing a stick, such as a cotton swab, into the registration paste before it has set to indicate the vertical and horizontal planes of the overlay with respect to the tooth plane. This placement was done with no visual representation of human teeth and as such could only provide approximation to the ideal position.

Another obstacle for a patient is the time needed for the preparation of a temporary overlay to be used while the permanent overlay is being manufactured. Often the temporary is made using a wax impression of the patient's original teeth. The teeth are then prepared for the overlay and the temporary is formed in place by using curing material. After the material is cured, it is then trimmed, polished and cemented in place. The problem with this procedure is that the patient remains with a look substantially like original teeth from the wax molding. The patient desires to have the look of the new veneer, while the permanent overlay is being prepared.

Temporary multi-tooth crown shells are known, but have only been applied to cuspid teeth and rearward for example the bicuspids and molars. Until now, there have been no full arched dental temporary that can also incorporate temporary crowns or temporary implants.

What is needed is a pre-fabricated demonstration dental template that can quickly be adhered to patients' teeth to demonstrate the look of a dental overlay for the patient. What is also needed is a dental prosthesis in the form of a dental template that provides the visual and tactile indicator to allow the consumer or patient to make a better educated decision prior to the onset of an aesthetic dental treatment; namely the application of a porcelain overlay. What is also needed is a method of visually demonstrating how a dental prosthesis can improve one's smile. Further, what is needed is a method to use the demonstration template also as a visual indicator to assist in determining the desired vertical and horizontal facial planes. The vertical plane determines how long the tooth should be with respect to the lips and other facial features. The overlay relative to the natural tooth plane can be set in a mold to maintain and be able to communicate information of the desired vertical and horizontal facial planes for the overlay relative to the natural teeth with the laboratory to facilitate ideal end results with respect to facial planes and symmetry.

What is needed is a full arched temporary pre-formed shell including front incisors that can be easily applied to a patient's prepared teeth as a temporary while the permanent overlay is being manufactured. What is also needed is a temporary shell that matches in size, shape and color of the demonstration template that is used on the patient.

SUMMARY OF THE DISCLOSURE

In accordance with one aspect of the invention, a demonstration dental template is in the form of a unitary substrate curved to conform to the extrados of the arch of a patient's natural teeth the dental template includes a rear surface shaped to abut against an outer side of patient's lower or upper teeth and to overlay on the patient's teeth. The template has a front exposed surface having visual representation of a plurality of real teeth. The proximate cervical edge often referred to as the cervical edge of the template defines the gum line with the teeth and a distal edge often referred to as an incisal (biting) edge defines the ends of the teeth.

The rear surface preferably has an adhesive thereon for temporarily adhering the template to the teeth of the patient. The adhesive strength should be weak enough to allow the dentist to easily pull the template off of the natural teeth. The adhesive may be a coating pre-applied to the template or applied in situ by the dentist.

In one embodiment, the substrate is an elastomeric material with a glazed three dimensional front surface simulating a porcelain surface to mimic the size, shape and texture of natural teeth. It is desirable that the incisal (biting) edge has a flange for extending about the natural tooth end. The substrate is flexible to allow the template to conform about any protruding teeth and to fit differently sized extradoses of the arches of the patent's natural teeth. In one embodiment, the pre-fabricated template is a dental template shaped to mimic at least the central incisors, lateral incisors, cuspids and first and second pre-molars, and first molar of the upper teeth. The template can be cut to remove any unneeded teeth such as for example second pre-molars, and first molars if they are initially part of the template but not under consideration for treatment.

In another embodiment, the demonstration dental template may be formed by a flat strip with a cervical edge having the shape of teeth at the gum line and the opposing incisal edge having the contour of incisal ends of the teeth crowns. The front side has shading to simulate individual teeth.

In this embodiment, the strip may have its front side simulating the central incisors, lateral incisors, cuspids, first pre-molars, second pre-molars and first molars and may be cut to remove unneeded teeth for a demonstration. The strip may be pre-cut and peelable from a protective backing. The strip may have a pre-applied adhesive backing that is protected by the protective backing.

In accordance with another aspect of the invention, a method visually demonstrating an improved smile to a dental patient includes the steps of temporarily placing a demonstration dental template to overlay in front of the teeth, preferably the upper teeth, of a patient, temporarily adhering the dental template to the natural teeth to allow removal of the dentist's or technician's hand to provide an unobstructed view of the demonstration template to the patient via a mirror, camera or other visual aid and removing the demonstration template from the natural teeth. The dental template extends from the gum line to the incisal (biting) edge of the natural teeth and shaped and surfaced to mimic the look of natural teeth.

The method preferably also includes placing the demonstration dental template over the central incisors, lateral incisors, cuspids and first pre-molars of the patient's upper teeth.

The method also preferably includes having a demonstration dental template being shaped to mimic and cover the central incisors, lateral incisors, cuspids, first pre-molars, second pre-molars and first molars and cutting off distal ends of the template if not needed for a patient's demonstration.

In accordance with another aspect of the invention, a method for setting the vertical and horizontal planes of a dental prosthesis overlay includes preparing natural teeth for the installation of a porcelain overlay; applying a setting material, for example a gel or paste generally referred to as a paste, to envelope the natural teeth to form a series of mold cavities lying in a tooth plane. A dental template is positioned on the paste at a desired vertical and horizontal facial planes such that the template appears vertical and horizontal relative to the vertical and horizontal facial planes for example with the top of head, forehead, eyebrows, eyes or cheekbones. The template is positioned on the paste at a desired vertical facial plane such that is pleasing to the eye and accepting of function.

The paste is set with the dental template in a set position to match the desired vertical and horizontal positions of the final porcelains or other prosthesis. The paste and template are then removed as an assembled unit from the natural teeth such that the paste mold cavities correspond in negative shape to the prepared natural teeth forming along the tooth plane and the dental template maintains its set position to record the position of the vertical and horizontal facial planes of the template relative to the tooth plane of the natural teeth. The assembled unit can be sent to the laboratory and used on the master model of prepared teeth to communicate desired vertical and horizontal of the overlay.

Preferably, a rear surface of the dental template is positioned onto the setting paste before the paste becomes set and the front surface of the template retains its visibility in front of the paste. It is desirable to align a plurality of individual upper teeth representation of the template in front of the individual natural teeth.

In accordance with one embodiment of the invention, a method for visually demonstrating an improved smile to a dental patient and setting the vertical and horizontal facial planes of a dental overlay includes temporarily placing a demonstration dental template to overlay in front of the teeth of a patient, temporarily adhering the dental template to the teeth to allow removal of the dentist's or auxiliary's hand to provide an unobstructed view of the demonstration template to the patient via a mirror, camera or other visual aid with the dental template extending from the gum line to the incisal crown ends of the teeth and shaped and surfaced to mimic the look of natural teeth. The demonstration dental template is then removed from the natural teeth, and natural teeth are prepared for the installation of a porcelain overlay. A setting paste is applied to envelope the natural teeth to form a series of mold cavities lying in a tooth plane of the natural teeth. The demonstration dental template is then positioned on the setting paste at a desired vertical and horizontal facial planes such that the template appears vertical and horizontal relative to the vertical and horizontal facial planes as previously mentioned. The paste is set with the demonstration dental template in a set position. The set paste and demonstration dental template are then removed as an assembled unit from the natural prepared teeth such that the paste mold cavities correspond in negative shape to the prepared natural teeth forming along the tooth plane and with the demonstration dental template maintains its set position to record the position of the facial plane of the template relative to the tooth plane of the natural teeth.

In accordance with another aspect of the invention, a mold for use in manufacturing a dental overlay includes a rear section having cavities corresponding in shape with natural teeth to be overlaid. The cavities lay along a first tooth plane corresponding to a tooth plane of the natural teeth. A front dental template section visually representing a plurality of individual teeth mounted at the front section of the paste mold with the front dental template aligned along a facial plane which may be canted with respect to the first tooth plane.

Preferably the mold has its rear section that has the cavities made from a setting paste and the front dental template section made from a plastic material. The front dental plastic material is affixed to the setting paste as it sets.

In accordance with another aspect of the invention, a dental demonstration and temporary overlay kit has a demonstration dental template with unitary substrate curved to conform to the extrados arch of a patient's natural teeth and a rear surface shaped to abut against an outer side of patient's lower or upper natural teeth and to overlay on the patient's natural teeth. The front exposed surface of the template has a visual representation of a plurality of natural teeth. The proximate upper edge of the demonstration dental template at an upper end of the visual representation of the plurality of natural teeth defines a gum line. A lower incisal edge of the demonstration dental template defines a tooth end. A temporary veneer overlay has a front surface matching in size and shape to the front exposed surface of the demonstrating template constructed for use as a temporary overlay on the patient's natural teeth after preparation of the patient's teeth for fitting an overlay. The temporary overlay preferably has its color matched to the color of the demonstration dental template. In one embodiment, the temporary overlay has a cavity for receiving the prepared teeth.

In accordance with another aspect of the invention, a dental demonstration and overlay kit has a demonstration dental template with a unitary substrate curved to conform to the extrados arch of a patient's natural teeth with a front exposed surface having a visual representation of natural teeth. A temporary veneer overlay has an outer surface matching the look of the front exposed surface of the demonstration template and constructed to fit over and bond to prepared teeth of the patient as a temporary overlay.

In accordance with another aspect of the invention, a temporary veneer overlay for use over a patient's natural teeth prepared for fitting an overlay has a full curve to conform to the extrados arch of a patient's teeth and a front section simulating a plurality of incisors. Preferably, the temporary overlay has sections simulating cuspids and bicuspids on each side of the plurality of incisors simulations. Preferably the temporary overlay has sections simulating molars and a cavity for receiving the prepared teeth.

In accordance with another aspect of the invention, a method for setting the vertical and horizontal planes of a dental prosthesis overlay and installing a matching temporary overlay includes the step of preparing natural teeth for the installation of a porcelain overlay. A setting paste is applied to envelope the prepared natural teeth to form a series of mold cavities lying along a tooth plane of the natural teeth. A dental template is then positioned on the paste at desired vertical and horizontal facial planes on the setting paste such that the template appears at a vertical appropriate position and also horizontal relative to the facial planes. The paste is set with the dental template in a set position. The set paste and template are then removed as an assembled unit from the prepared natural teeth such that the paste mold cavities correspond in negative shape to the natural teeth forming along the tooth plane and with the dental template maintaining the set position to record the position of the vertical and horizontal facial planes of the template relative to the tooth plane of the natural teeth. A temporary overlay that has an interior cavity then has its cavity filled with a curing agent. The temporary overlay has simulated teeth that match the look of the dental template. The temporary overlay is placed over or against the prepared teeth and the curing agent relines and cures to temporarily bond the temporary overlay with the prepared teeth.

BRIEF DESCRIPTION OF THE DRAWINGS

Reference now is made to the accompanying drawings in which:

FIG. 1 is a perspective view of a dental template in accordance with one embodiment of the invention;

FIG. 2 is a top plan view of the dental template as shown in FIG. 1;

FIG. 3 is front elevational view of the dental template as shown in FIG. 1;

FIG. 4 is a cross-sectional view taken along lines 4-4 shown in FIG. 1;

FIG. 5 is a front view of a patient's smile before use of the dental template;

FIG. 6 is a front view demonstrating use of the dental template on a patient;

FIG. 7 is the front elevational view of an alternative embodiment disclosing the invention;

FIG. 11 is a cross sectional view of the lower template taken along FIG. 11-11 shown in FIG. 6;

FIG. 16 is a top plan view of a temporary overlay to illustrate the internal cavities 122 according to an embodiment of the invention;

FIG. 17 is a front elevational view of the overlay shown in FIG. 16;

FIG. 18 is a cross sectional view taken along lines 18-18 shown in FIG. 17;

FIG. 19 is a cross sectional view taken along lines 19-19 shown in FIG. 16; and

FIG. 20 is a view similar to FIG. 18 showing the temporary overlay installed and bonded to a patient's prepared teeth.

DETAILED DESCRIPTION OF THE PREFERRED EMBODIMENT

Figure 8:
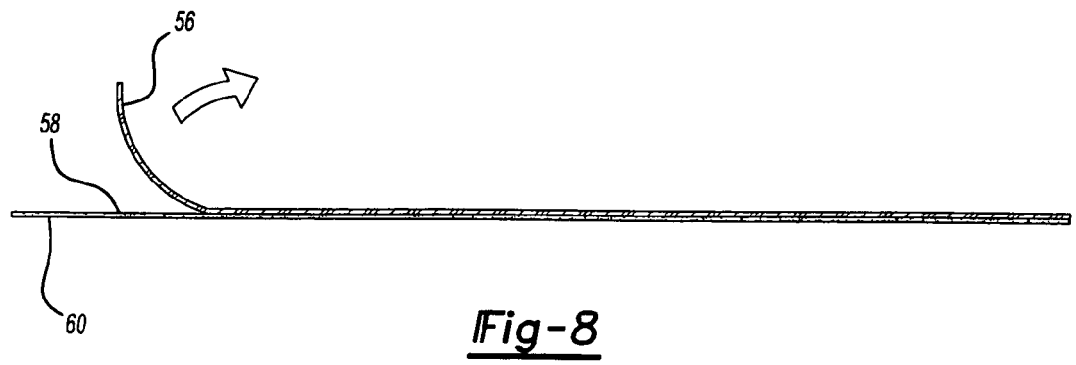
FIG. 8 is a top plan view of the embodiment shown in FIG. 7 showing the teeth peeled from its protective backing.
Figure 9:
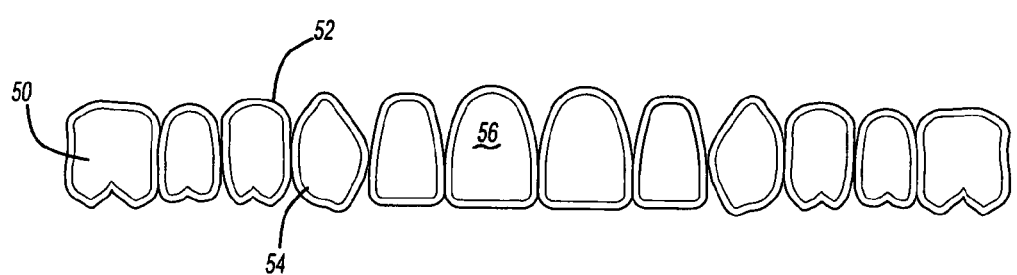
FIG. 9 is a elevational view of the embodiment shown in FIG. 7 with the front teeth removed from the backing.

Referring now to FIG. 1, a dental template 10 is shown that simulates natural teeth of a patient. Dental template 10 is made from urethane or Santoprene™ material and is shaped to be positioned to abut against the front surface of a patient's natural teeth 40 shown in FIG. 5. Front surface 12 of the template has a finished porcelain look to simulate natural teeth. The front surface 12 is scalloped to mimic the natural division of individual teeth such as the front central incisors 14, lateral incisors 16, cuspids 18, first premolars 20, second premolars 22 and first molars 24.

Top edge 26 of the dental template 10 is contoured to simulate the top of natural teeth to define the gum line. The incisal bottom edge 28 of the dental template simulates the incisal (or biting) end of the upper teeth. The biting (incisal) edge 28 as shown more clearly in FIGS. 3 and 4 forms a lip or ledge 30 to rest on the existing biting edge. The rear surface 32 is contoured with a generally flat-to-slightly concave negative shape to abut the individual natural teeth of the patient.

The urethane or Santoprene™ material allows the template to flex to match the extrados of the arch of the patient's natural teeth 40 and to abut against the patient's natural teeth 40. Other suitable flexible plastics or elastomeric materials with similar sanitary and flexible qualities can also be utilized in place of the urethane or Santoprene™. A temporary adhesive or glue for example a bite registration paste can be placed on the back surface 32 to retain the dental template in position against the patient's teeth 40 during inspection or examination. The adhesive may be pre-applied onto the template or may be applied in situ by the dentist or auxiliary personnel.

The dental patient or prospective dental patient can visually inspect the appearance of this dental template 10 in his mouth via a mirror. And can view the template from a variety of angles. In addition to the three dimensional visual aspect of the dental template the demonstration can provide indication of how a permanent porcelain will feel against the front surface of his natural teeth and lips during different smiles, biting and lip motions. As shown in FIGS. 5 and 6 the patient and prospective patient can quickly see the difference between his natural teeth 40 and natural smile with a smile that includes a porcelain overlay by looking at template 10 in position. FIG. 5 illustrates natural teeth with misaligned and chipped teeth as well as asymmetrical gum heights or gum lines 27 and 29.

The method of demonstrating an improved smile to the patient becomes expeditious and time efficient. Providers such as a dentist, dental hygienist or other auxiliary personnel can merely place the dental template against the natural teeth of the patient. As shown in FIGS. 5 and 6, the dental template may extend over a low gum line 27 illustrates on the left side of FIG. 5 to the incisal edge (biting edge) end 28 of the crown at the lower edge above the patient's natural teeth with the flange 30 wrapped around or ending beyond the edge of the patient's natural teeth. This indicates to the dentist that some gum may be removed to raise the gum line. On the other hand, as shown on the right side of FIG. 6, if a high gum line 29 remains visible behind and above gum line 26 of the template, gum can be added back to lower the gum line 29 to create a symmetrical gum height as demonstrated by gum line 26 of the demonstration template 10. The template can be temporarily adhered to the teeth to allow the patient and prospective patient to inspect them dynamically in position. The patent can smile in a variety of ways and even talk while the template is in position. After inspection is over, the dental template is merely removed from the patient's or prospective patient's mouth and his teeth. As an option, because of the ease of insertion and removal of the template, the patient can leave the office with the template to insert at home to show a spouse or loved one for reassurance and decision making. This allows the consumer and potential patient to make a better educated decision prior to the commencement of aesthetic dental procedures, namely the application of dental porcelains.

The template can be manually maneuvered and placed in position by the dentist, technician or lay person. A mere grasping with a forefinger and thumb is often all that is needed to successfully place the template in position. Another installation device besides a hand is also foreseen to be used with this template.

Single and multiple combinations of shorter segments of the dental template can be used to illustrate smaller applications. In some instances, the first molars, second premolars, and first pre molars and possibly the cuspids may not be needed to improve patient's smile. In these cases, the dental template is cut at one of the defined interstices 34. For example, there may be instances, where the demonstration dental template has only the central incisors, lateral incisors, cuspids and first premolars. The rearward posterior teeth, i.e. the second premolars and first molars may be cut off the template 10 and discarded.

The removal of the template is also quick and easy. The temporary adhesive should be of a known type that provides a relatively weak securement so that a manual pull on the template will remove it from the natural teeth. The adhesive may be of the same type that secures temporary crowns or inlays in place or be such that is used as a bite registration material.

Figure 10:
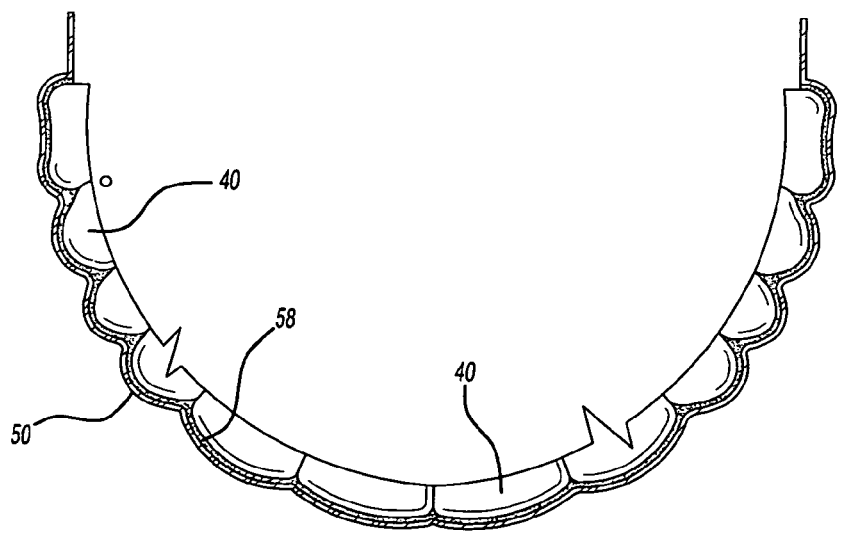
FIG. 10 is a top plan view of the alternative embodiment showing the strip in position against the natural teeth of a patient.

Another embodiment is shown in FIGS. 7-10. In the second embodiment, the dental template comprises a flat strip 50 that has contoured top and bottom edges 52 and 54. And the front surface 56 is photographed or shaded to simulate individual teeth and an adhesive backing 58 to adhere to the front teeth of the patient. The strip can be packaged flat and be peelable from a protective backing 60 that allows the adhesive backing to be easily peeled from the rear surface 58. The strip 50 is flexible to fit about the extrados of the arch of the natural teeth 40 and follow the general contour of each individual tooth 40 as shown in FIG. 10.

The dental templates may be prefabricated in various sizes, styles and shades to better fit and cosmetically blend with different sized mouths and varying types and shades of teeth. The use of the dental template on the front upper teeth may quickly give a visual and tactile indicator to allow the consumer and potential patient to make a better educated decision prior to the commencement of an aesthetic dental treatment namely the application of a dental overlay.

Templates 10' as shown in FIGS. 6 and 11 are also foreseen to be used on occasion with lower teeth. If the template 10' is made for lower teeth, care needs to be directed to make the template 10' thin enough as with the permanent porcelain overlay so as not to interfere with the patient's bite. The lower dental template 10' would also have its incisal end 28' wrap further over the incisal end of the lower teeth to keep the edge 30' of the template hidden from normal viewing angles of the lower arch.

The temporary installation of the template is simple enough that any of the above described embodiments can also be disseminated to potential patients as a mail piece for installation by a lay person in order to intrigue the prospective patient. The use of the three dimensional or flat sticker embodiments may be used by dentists or dental laboratories to heighten consumer awareness and to instigate a prospective patient to make an appointment for a consultation to further investigate the feasibility of specific smile enhancement options through cosmetic surgery.

Figure 12:
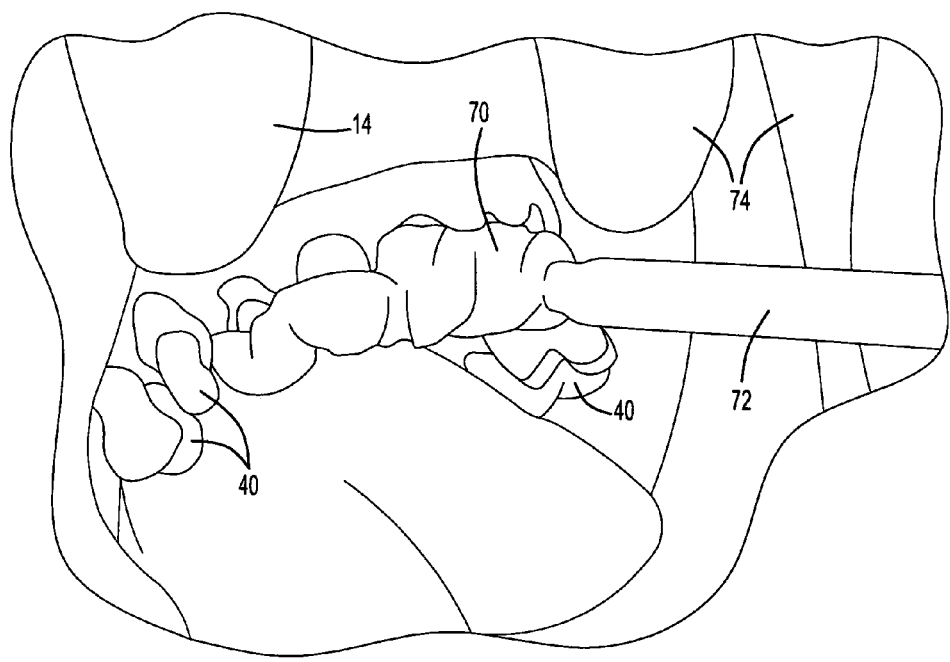
FIG. 12 is a view of paste being set onto prepared natural teeth.

The dental template can also be subsequently used to set the vertical and horizontal planes of the overlay when a patient decides to proceed with the cosmetic overlay. The patient has the natural teeth shaped and prepared to receive an overlay. After the natural teeth are properly shaped, a setting gel or bite registration paste 70 is placed to completely surround the prepared natural teeth 40 as shown in FIG. 12 such that an impression of the teeth 40 is made in the paste. The paste is delivered by a conventional applicator 72. A clear bite registration paste such as Crystal Clear by Clinicians Choice is suitable. However, the paste may be any of a variety of commercially available bite registration pastes. Blue Mousse by Parkell and Memosil 2 by Heraeus-Kulzer GmbH and Co. KG are two other suitable pastes. Other gels and pastes are also foreseen to be suitable.

Figure 13:
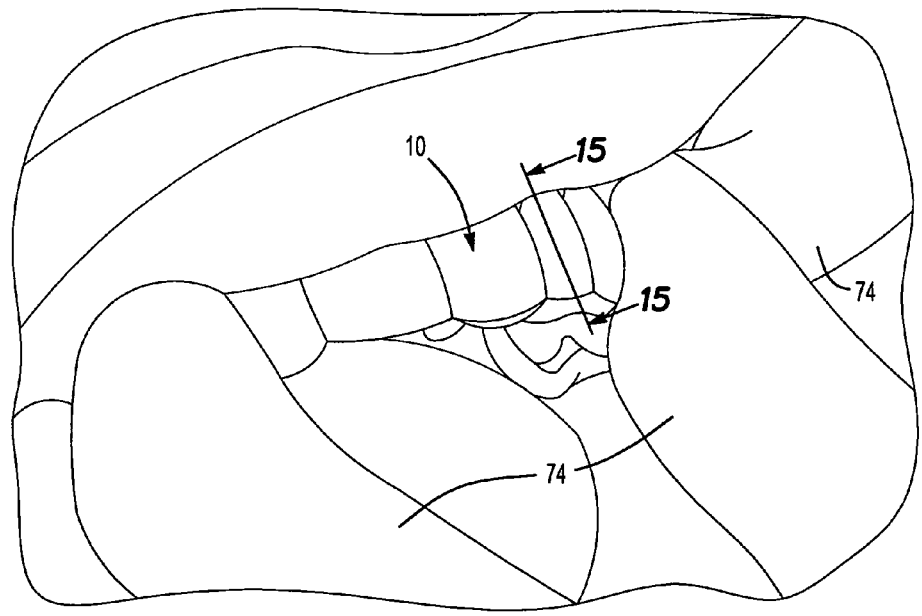
FIG. 13 is a perspective view of a dentist or auxiliary personnel applying the demonstration dental template positioned onto and affixed to the paste.
Figure 14:
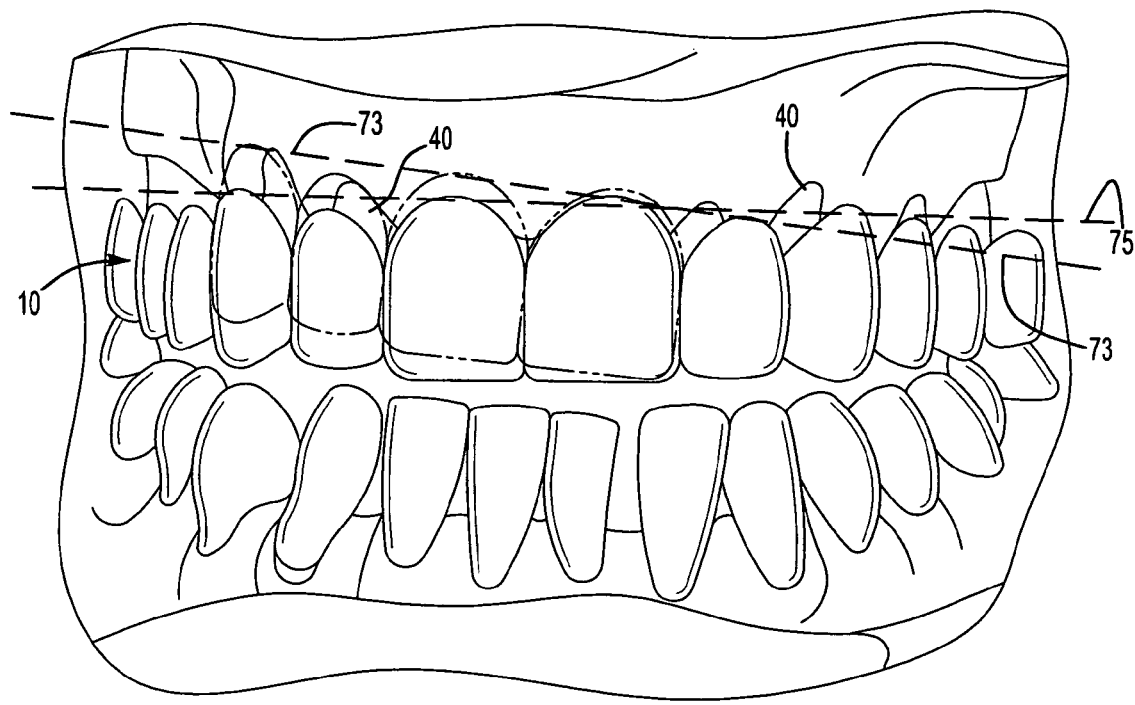
FIG. 14 is a partially schematic view illustrating a situation where the dental template is aligned with vertical and horizontal facial planes and is canted with respect to the natural tooth plane.

While the paste is setting, the dental template 10 is then placed on the paste as shown in FIG. 13. The template 10 floats on the registration paste 70 and can be manually moved by the dentist or auxiliary personnel by pressure from his fingers 74. As illustrated in FIG. 14, the template 10 may be vertically and horizontally positioned at an angle 75 compared to the natural tooth plane indicated as 73. The template angle 75 may be set at an angle that provides the best appearance for the overlay. The best vertical and horizontal facial planes may be visually determined by taking into account many vertical and horizontal planes of the face, i.e. the top of the head, the forehead, the eyebrow plane, the plane of the eyes, the plane of the cheek bones and the upper and lower lip angles and lower jaw. The best vertical plane can be decided upon based on lip position at rest and high-or-low smile lines. At rest, it is desirable to see 1-2 mm of incisal length of the maxillary central.

Figures 15A, 15B:
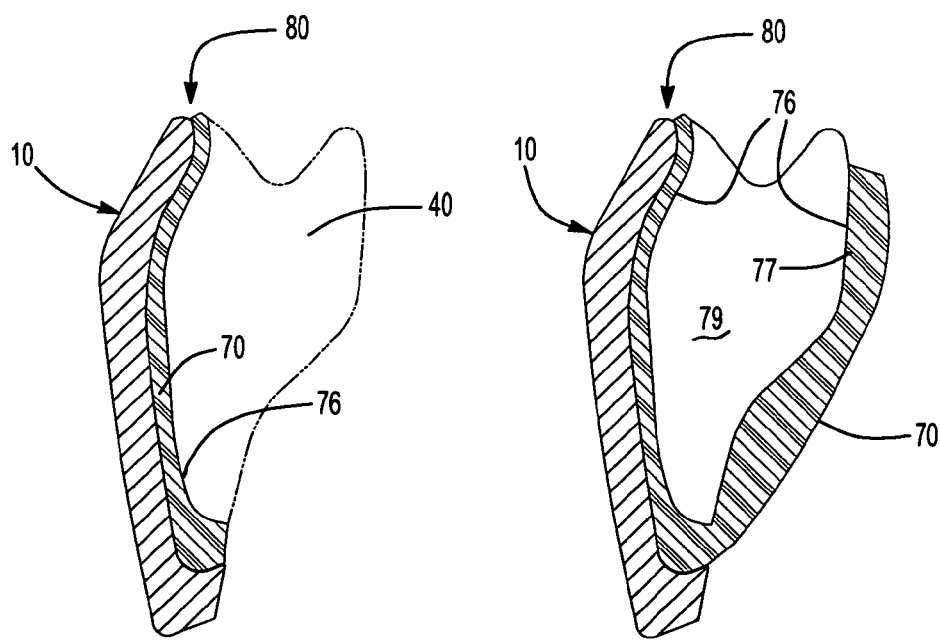
FIG. 15(a) is a cross-sectional view taken along lines 15-15 in FIG. 13 illustrating the mold formed from the set paste and the front dental template for situation where only front exterior surface of the teeth needed preparation.
FIG. 15(b) is a view similar to FIG. 15(a) where the tongue side of the teeth have also been prepared and a mold for a full veneer on both sides is formed.

Once the dentist sets the planes and confers with the patient that the template 10 is at the best vertical and horizontal facial planes, the paste 70 is then allowed to set with the template 10 in the set angle as shown in FIG. 14. Once the paste is set, the template is now securely affixed in place to the paste and the mold assembly 80 can be removed from the teeth 40 by gently pulling it away from the teeth. As shown in FIG. 15(a), the mold 80 may just cover the exterior front surface of the natural teeth 40 to the incisal biting edge and form a inner surface 76 to the prepared front surface of the teeth 40. As shown in FIG. 15(b), the mold may extend over the tongue side of the teeth 40 to form a back side 77 of mold 80 and forms a cavity 79 within mold 80. In other cases, the mold 80 formed by the template 10 and the registration paste 70 can be shipped off to the lab for manufacturing the overlay. The paste 70 has its inner surfaces 76 that individually correspond to the natural teeth 40 and in series lie in the tooth plane 73. The template is affixed at the desired facial angle 75 independent from tooth plane 73. This desired facial angle can then be transferred to the working model to demonstrate to the laboratory technician the desired cant and length at which the porcelains or other restorations should be manufactured.

In this fashion, all information as to the tooth plane and facial plane are easily communicated to the technician of the overlay with a dental template. The dental template 10 has multiple purposes. Firstly, to demonstrate the appearance of an overlay. Secondly, it helps visually to determine the appropriate facial plane in which the overlay should follow. Thirdly, the prepared mold communicates to the lab the appropriate facial angle of the overlay relative to the tooth plane to establish vertical and horizontal tooth planes with ultimately ideal aesthetic results.

For prepared teeth and a mold as shown in FIG. 15(b), the patient can be fitted with a temporary full veneer overlay 110 available for more difficult situations. As shown in FIGS. 16-20, the full veneer 110 that is sized, shaped and colored to match template 10 so the patient may have the new desired look and shape of new teeth while waiting for the manufacture and installation of the permanent porcelain veneer overlay.

The temporary overlay 110 as shown in FIG. 16 includes a plurality of simulated teeth sections, for example simulated incisor sections 112, simulated cuspid sections 114, simulated bicuspid sections 116 and simulated molar sections 118. The overlay 110 has each section 112, 114, 116, and 118 with its outer front surface 120 simulating natural teeth as shown and demonstrated by the dental template 10. As such, the dental template 10 and temporary overlay 110 can be packaged and sold together as a kit. The size, shape and color of each template 10 is matched by a corresponding temporary overlay 110 as shown by comparison FIG. 17 with FIG. 1.

The overlay 110 also has each section 112, 114, 116 and 118 with a front exterior wall 130, rear wall 132 and interior cavities 122 therebetween as shown in FIGS. 18 and 19 sized to receive the prepared natural teeth 40 of the patient. When the temporary overlay 110 is installed, it may be relined with suitable curable material 128 to fill any space between the overlay 110 and the prepared natural teeth 40. The front and rear walls 130, 132 are joined at the distal end to form a properly shaped biting edge 134 below cavity 122. The biting edge 134 is shaped to correctly correspond to the respective incisor, cuspid, bicuspid or molar section 112, 114, 116, 118. The overlay 110 may be made from a suitably temporary crown or overlay material for example, methyl methacrylate or an acrylic resin. As shown in FIG. 20, the interior cavity 127 can be relined and filled with suitable curing and bonding material 126 to intimately fit the temporary overlay 110 to the prepared patient's teeth 40.

The overlay 110 is strong enough to provide one or more sections to act as a temporary crown, bridge or implant to fill any gap in-between the prepared teeth 40. While overlay 110 is made to cover both the front and rear side of a prepared tooth for molds shown in FIG. 15(b), there may be occasions when only the front side of the natural teeth need preparing as shown in FIG. 15(a). In these situations, a temporary may be shaped identically as the demonstration template 10 shown in FIGS. 1-4 to be adhered only onto the prepared front of the natural teeth. This front temporary is made from the same suitably temporary material, for example methyl-methacrylate or an acrylic resin.

For either situation, the patient has a temporary that provides for a cosmetic improvement over the natural teeth 40 that closely matches the original demonstration template in size, appearance and color while waiting for the permanent veneer to be manufactured.

Other variations and modifications are possible without departing from the scope and spirit of the present invention as defined by the appended claims.

The embodiments in which an exclusive property or privilege is claimed are defined as follows:

1. A dental demonstration and temporary overlay kit comprising:
   a demonstration dental template having unitary substrate curved to conform to the extrados arch of a patient's natural teeth, a rear surface shaped to abut against an outer side of patient's lower or upper natural teeth and to overlay on the patient's natural teeth, a front exposed surface of the demonstration dental template having visual representation of a plurality of natural teeth, a proximate upper edge of said demonstration dental template shaped to mimic the shape of a desired cervical margin of said teeth at a gum line, a lower incisal edge of said demonstration dental template defining ends of a plurality of teeth, said demonstration dental template being flexible to conform about any protruding teeth and to fit different sized extradoses of the natural teeth of a plurality of patients; and a temporary veneer overlay having a front surface matching in size and shape to the front exposed surface of said demonstration dental template made from a rigid strong material to withstand biting forces that is different from the material of the demonstration dental template and for use as a temporary overlay on said patient's natural teeth after preparation of said patient's teeth for fitting an overlay.

2. A dental demonstration and overlay kit as defined in claim 1 further comprising:

said temporary veneer overlay matching its color to the color of said demonstration dental template.

3. A dental demonstration and overlay kit as defined in claim 2 further comprising:

said temporary veneer overlay having a cavity therein for receiving respective prepared natural teeth.

4. A dental demonstration and overlay kit comprising:

a demonstration dental template made from a plastic or elastomeric material having a unitary substrate curved to conform to the extrados arch of a patient's natural teeth with a front exposed surface having a visual representation of natural teeth and being flexible to conform to irregularities, spacings, and protrusions of said patient's natural teeth; and a temporary veneer overlay made from a temporary crown or overlay material different from the plastic or elastomeric material of the demonstration dental template and having a rigidity and strength to withstand said patient's biting forces, having an outer surface matching the look of the front exposed surface of the demonstration dental template and constructed to fit with and bond to prepared teeth of the patient as a temporary overlay.

5. A dental demonstration and overlay kit as defined in claim 4 further comprising:

said temporary veneer overlay having a cavity therein for receiving respective prepared natural teeth.

6. A method for setting the vertical and horizontal planes of a dental prosthesis overlay and installing a matching temporary overlay comprising:

preparing natural teeth for the installation of a porcelain overlay;

applying a setting paste to envelope said prepared natural teeth to form a series of mold cavities lying along a tooth plane of said natural teeth;

positioning a dental template on a front side of said paste at a desired vertical plane and a desired horizontal facial plane such that said dental template appears vertical and horizontal relative to the vertical and horizontal facial planes;

setting said paste with said dental template in a set position;

removing said paste and dental template as an assembled unit from said prepared natural teeth such that said mold cavities correspond in negative shape to said natural teeth forming along said tooth plane and with said dental template maintaining the set position to record the position of the vertical and horizontal facial planes of the dental template relative to the tooth plane of said natural teeth;

filling a cavity in a temporary overlay which has simulated teeth that match the look of said dental template with a curing agent and placing the temporary overlay over the prepared teeth; and curing the curing agent to temporarily bond the temporary overlay with said prepared teeth.

7. A method setting the horizontal plane of a dental prosthesis overlay comprising:

preparing natural teeth for installation of a porcelain overlay;

applying a setting paste to envelope said prepared natural teeth by covering both the lingual and buccal surfaces of the prepared natural teeth to form a series of mold cavities lying along a tooth plane of said natural teeth with a wall section touching the lingual surface of said teeth and a second wall section touching the buccal surface of said teeth;

positioning a dental template on a front side of said paste at a desired horizontal facial plane such that said dental template appears horizontal relative to the horizontal facial plane with said dental template having a proximate edge substantially free of material positioned beyond said proximate edge over a patient's gum such that a patient's gum is visible from the front when the dental template is in position in a patient's mouth;

setting said paste with said dental template in a set position; and removing said paste and dental template as an assembled unit from said prepared natural teeth such that said mold cavities correspond in negative shape to said natural teeth forming along said tooth plane and with said dental template maintaining the set position to record the position of the horizontal facial plane of the dental template relative to the tooth plane of said natural teeth.

8. A method as defined in claim 7 further comprising:

positioning a rear surface of said dental template onto said setting paste before said paste becomes set; and retaining the front surface of said dental template visible in front of said paste.

9. A method as defined in claim 8 further comprising:

aligning a plurality of individual upper teeth representation of said dental template in front of said individual natural teeth.

10. A mold for use in manufacturing a dental overlay said mold comprising:

a rear section having a wall section for touching a lingual surface of prepared natural teeth and a second wall section for touching a buccal surface of said prepared natural teeth and forming cavities corresponding in shape with prepared natural teeth and lying along a first tooth plane corresponding to a tooth plane of said natural teeth;

a front dental template section representing a plurality of individual teeth affixed to said rear section, said front dental template section set in a facial plane independent with respect to said first tooth plane formed by said cavities;

said front dental template section having a proximate edge being substantially free of material beyond said proximate edge over a patient's gum so that patient's gum is visible from the front of said mold when in position in said patient's mouth;

said rear section made from a setting paste; and said front dental template section made from plastic or elastomeric material affixed to said setting paste as it sets.

11. A method setting the horizontal plane of a dental prosthesis overlay comprising:
   preparing natural teeth for the installation of a porcelain overlay;
   applying a setting paste to said prepared natural teeth to form a series of negative surfaces corresponding to the buccal side of the prepared natural teeth lying along a tooth plane of said natural teeth;
   positioning a dental template on said paste at a desired horizontal facial plane such that said dental template appears horizontal relative to the horizontal facial plane with said dental template having a proximate edge shaped to mimic a desired cervical margin of natural teeth;
   said proximate edge being substantially free of material beyond it over a patient's gum such that said patient's gum or teeth are visible from the front when the dental template is set on said setting paste in patient's mouth;
   setting said paste with said dental template in a set position; and
   removing said paste and dental template as an assembled unit from said prepared natural teeth such that said negative surfaces correspond in negative shape to the buccal side of said natural teeth forming along said tooth plane and with said dental template maintaining the set position to record the position of the horizontal facial plane of the dental template relative to the tooth plane of said natural teeth.

* * * * *